United States Patent
Burton

(10) Patent No.: US 8,303,539 B2
(45) Date of Patent: Nov. 6, 2012

(54) PREFORM AND BALLOON HAVING A NON-UNIFORM THICKNESS

(75) Inventor: David G Burton, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 23 days.

(21) Appl. No.: 12/788,829

(22) Filed: May 27, 2010

(65) Prior Publication Data

US 2010/0234874 A1    Sep. 16, 2010

Related U.S. Application Data

(62) Division of application No. 12/015,315, filed on Jan. 16, 2008, now Pat. No. 7,753,875.

(60) Provisional application No. 60/897,202, filed on Jan. 24, 2007.

(51) Int. Cl.
*A61M 37/00* (2006.01)

(52) U.S. Cl. .................................. 604/103.08

(58) Field of Classification Search ............ 604/103.07, 604/103.08; 606/185, 194; 623/1.11
See application file for complete search history.

(56) References Cited

U.S. PATENT DOCUMENTS

| | | | |
|---|---|---|---|
| 2,078,686 A * | 4/1937 | Rowe | 604/103.02 |
| 4,738,666 A | 4/1988 | Fuqua | |
| 5,295,994 A | 3/1994 | Bonutti | |
| 5,295,995 A * | 3/1994 | Kleiman | 606/194 |
| 5,318,587 A | 6/1994 | Davey | |
| 5,456,666 A | 10/1995 | Campbell et al. | |
| 5,792,172 A | 8/1998 | Fischell et al. | |
| 5,792,300 A * | 8/1998 | Inderbitzen et al. | 156/244.13 |
| 6,544,224 B1 * | 4/2003 | Steese-Bradley | 604/103.06 |
| 6,875,197 B1 | 4/2005 | Simhambhatla et al. | |
| 7,226,475 B2 * | 6/2007 | Lenz et al. | 623/1.16 |
| 7,491,188 B2 | 2/2009 | Holman et al. | |
| 7,753,875 B2 * | 7/2010 | Burton | 604/103.06 |
| 2004/0215223 A1 | 10/2004 | Shaw et al. | |
| 2005/0123640 A1 | 6/2005 | Mahoney et al. | |
| 2006/0079836 A1 | 4/2006 | Holman et al. | |
| 2009/0099588 A1 | 4/2009 | Makower et al. | |
| 2010/0241178 A1 * | 9/2010 | Tilson et al. | 606/86 R |

OTHER PUBLICATIONS

Haq-Munoz, Sakeena, et al. "Plastic Formations of All", presentation by Sandy Van Natta at the MATR Institute, 1997, 3 pgs.
Sauerteig, Knut, et al. "The Effect of Extrusion and Blow Molding Parameters on Angioplasty Balloon Production" *Medical Plastics and Biomaterials Magazine*, published May 1998, 10 pgs.

(Continued)

*Primary Examiner* — Nicholas Lucchesi
*Assistant Examiner* — Diva K Chander
(74) *Attorney, Agent, or Firm* — Brinks Hofer Gilson & Lione

(57) ABSTRACT

The present invention provides a balloon having a non-uniform thickness that is adapted to facilitate folding of the balloon. The balloon comprises at least one relatively thin section formed between inner and outer surfaces of the balloon, and at least one relatively thick section formed between the inner and outer surfaces. The balloon may be formed from a balloon preform that similarly comprises at least one relatively thin section and at least one relatively thick section. The shape of the balloon preform may be formed, for example, by extrusion. The balloon preform may be placed in a balloon mold having a substantially cylindrical interior surface, and blow-molded to form the finished balloon configuration. The balloon comprises a non-uniform thickness, while comprising a substantially cylindrical outer diameter both after removal from the balloon mold and in an inflated state.

13 Claims, 2 Drawing Sheets

OTHER PUBLICATIONS

*Angioplasty Balloon—Background, History, Raw Materials, The Manufacturing Process* . . . Angioplasty Balloon forum: How Products Are Made vol. 6, http://www.madehow.com/Volume-6/Angioplasty-Balloon.html, webpage last visited Dec. 8, 2006, 6 pgs.

\* cited by examiner

PREFORM AND BALLOON HAVING A NON-UNIFORM THICKNESS

PRIORITY CLAIM

The present patent document is a divisional application that claims the benefit of priority under 35 U.S.C. §121 of U.S. patent application Ser. No. 12/015,315, filed Jan. 16, 2008, which is hereby incorporated by reference in its entirety.

This invention claims the benefit of priority of U.S. Provisional Application Ser. No. 60/897,202, entitled "Preform and Balloon Having a Non-Uniform Thickness," filed Jan. 24, 2007, the disclosure of which is hereby incorporated by reference in its entirety.

BACKGROUND

The present invention relates generally to apparatus and methods for treating vascular conditions, and more specifically, to a balloon having a non-uniform configuration that improves the folding capability of the balloon after it is deflated.

Atherosclerosis and other occlusive diseases are prevalent among a significant portion of the population. In such diseases, atherosclerotic plaque forms within the walls of the vessel and blocks or restricts blood flow through the vessel. Atherosclerosis commonly affects the coronary arteries, the aorta, the iliofemoral arteries and the carotid arteries. Several serious conditions may result from the restricted blood flow, such as ischemic events.

Various procedures are known for treating stenoses in the arterial vasculature, such as balloon angioplasty. During a balloon angioplasty procedure, a catheter having a deflated balloon attached thereto is inserted into a patient's vessel. In some cases, it is desirable to introduce the balloon in a configuration whereby the balloon is twisted or folded upon itself in order to reduce the radial profile of the balloon during delivery. Once positioned across a constricting lesion, the balloon then is inflated to widen the lumen to partially or fully restore patency to the vessel. After satisfactory widening of the stenosis has been achieved, the balloon is deflated. The catheter then is retracted and removed from the patient's vessel with the balloon in the deflated state.

One problem that exists with conventional angioplasty balloons is that they may not collapse reliably after deflation. For example, after the balloon is expanded to engage the vessel wall and then deflated, the balloon may obtain a flattened configuration, e.g., having two opposing regions that extend radially outward. In those cases, it may be difficult to withdraw the balloon from the patient's vessel. If an introducer sheath is used, the balloon may become caught within the sheath upon retraction and removal.

At least one previously-known device has attempted to reduce the profile of a balloon in the deflated state by providing a non-uniform balloon wall thickness around the balloon circumference, thereby forming a deflated wing when the balloon is deflated. In particular, U.S. Pat. No. 6,544,224 to Steese-Bradley (hereinafter "the '224 patent") discloses a balloon comprising a lobular outer surface after formation in a balloon mold. The balloon disclosed in the '224 patent is formed by providing a cylindrical balloon preform, and blow-molding the balloon preform within a mold having lobular or concave-shaped interior surfaces. Therefore, after it is formed, the balloon assumes a lobular-shaped outer surface, and has a non-uniform wall thickness about a portion of its circumference. The molded, non-uniform balloon of the '224 patent therefore comprises a substantially different shape compared to the uniform, cylindrical balloon preform. Moreover, the formation of the non-uniform wall thickness of the balloon of the '224 patent is based upon the provision of the non-cylindrical interior surface of the balloon mold.

In view of the foregoing, there is a need for a balloon that achieves a sufficiently collapsed radial profile after deflation in order to reduce the likelihood that the balloon will become caught upon removal from the patient's vessel.

SUMMARY

The present invention provides a balloon having a non-uniform thickness that may comprise a reduced profile in a deflated state. The balloon may be formed from a balloon preform having a non-uniform thickness that is substantially proportionally identical to the shape of the formed, inflated balloon. The balloon preform may be formed into the balloon using a balloon mold comprising a substantially cylindrical interior surface. Therefore, the formed balloon comprises a substantially cylindrical outer diameter after formation by the balloon mold.

In a first embodiment, the balloon comprises inner and outer surfaces, and has inflated and deflated states. At least one relatively thin section having a first thickness is formed between a portion of the inner and outer surfaces. Further, at least one relatively thick section having a second thickness is formed between another portion of the inner and outer surfaces. The second thickness is greater than the first thickness along a portion of the circumference of the balloon.

In one embodiment, the balloon is comprised of three relatively thin sections and three relatively thick sections disposed about the circumference of the balloon, wherein each relatively thin section is disposed circumferentially between a relatively thick section. In operation, the variable thickness between the relatively thin sections and the relatively thick sections may allow the balloon to achieve a reduced diameter profile, for example, by promoting folding of the balloon into at least two wings in the deflated state.

In accordance with one aspect, the balloon may be formed from a balloon preform having a non-uniform thickness that is substantially proportionally identical to the shape of the balloon. Like the balloon, the balloon preform similarly comprises an inner surface, an outer surface, at least one relatively thin section formed between the inner and outer surfaces, and at least one relatively thick section formed between the inner and outer surfaces. The balloon preform may be extruded to form the relatively thin sections and the relatively thick sections, while maintaining a substantially cylindrical outer surface.

In one exemplary technique, the balloon preform is formed into the balloon using a balloon mold having a substantially cylindrical interior surface. The balloon preform may be blow-molded to expand to form the balloon. Since the balloon mold comprises a substantially cylindrical interior surface, the formed balloon comprises a substantially cylindrical outer diameter after formation in the balloon mold, and further comprises a substantially cylindrical outer diameter in the inflated state during treatment of a vessel. Further, the non-uniform thickness of the balloon, due to the non-uniform thickness of the balloon preform, is adapted to facilitate folding of the balloon upon deflation.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
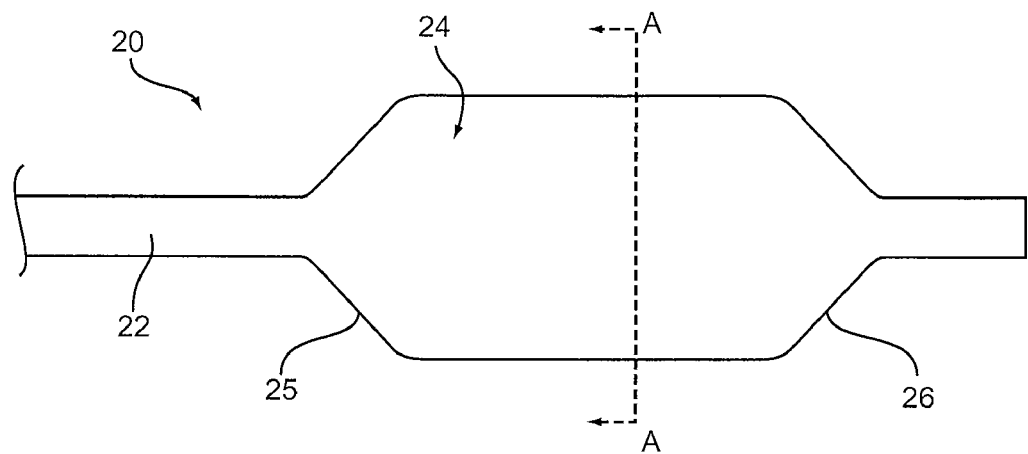
FIG. 1 is a side view of a balloon catheter having a balloon provided in accordance with a first embodiment.
Figure 2:
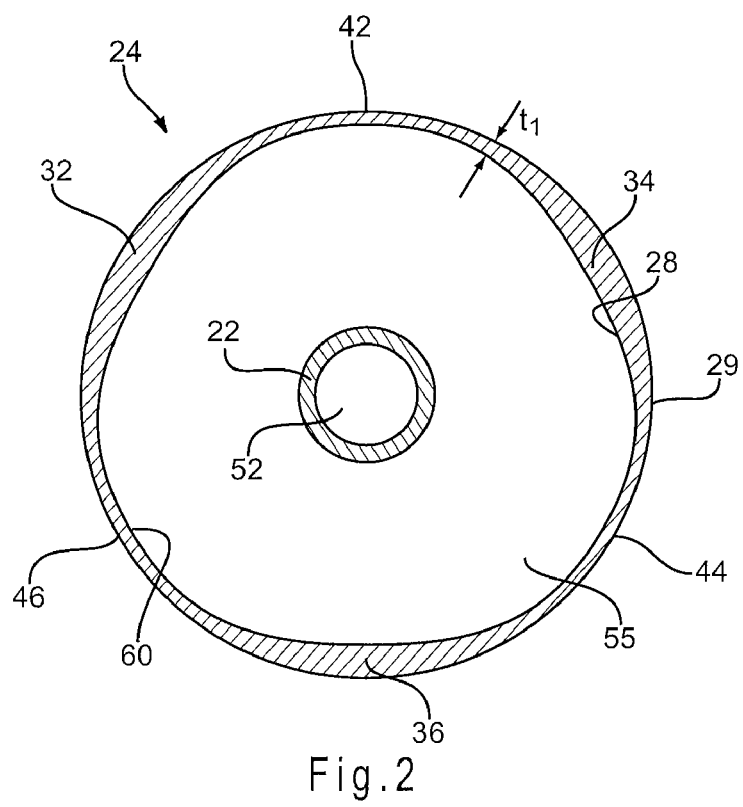
FIG. 2 is a cross-sectional view of the balloon taken along line A-A of FIG. 1.

Referring now to FIGS. 1-2, a first embodiment of a balloon catheter having an improved balloon folding capability is described. In FIG. 1, balloon catheter 20 comprises catheter 22 having proximal and distal regions, and balloon 24 disposed on the distal region. In this embodiment, balloon 24 comprises tapered proximal region 25, which may be affixed at a first location to an exterior surface of catheter 22. Similarly, balloon 24 is shown having tapered distal region 26, which may be affixed at a second location to the exterior surface of catheter 22. Alternatively, distal region 26 may be affixed to a separate tube, such as an inner tube that is disposed coaxially within catheter 22 and extends distally therefrom.

Catheter 22 may comprise a flexible, tubular member that may be formed from one or more semi-rigid polymers. For example, the catheter may be manufactured from polyamide, polyurethane, polyethylene, tetrafluoroethylene, polytetrafluoroethylene, fluorinated ethylene propylene, or the like.

Balloon 24 may be manufactured from any suitable balloon material used during an interventional procedure, such as an angioplasty procedure. For example, balloon 24 may be manufactured from a material such as PEBAX, nylon, Hytrel, Arnitel, or other polymers. The shape of balloon 24 may be formed, for example, by blow-molding balloon preform 124 within balloon mold 200, as explained in greater detail below with respect to FIGS. 3-4 below.

After formation, balloon 24 is attached to the distal region of catheter 22. For example, proximal and distal regions 25 and 26 of balloon 24 may be affixed to the exterior surface of catheter 22 using any suitable adhesive, such as biocompatible glue, or alternatively, using heat-shrink tubing, heat bonding, laser bonding, welding, solvent bonding, one or more tie-down bands, or the like. It is preferred to use a bonding technique that enables melting of balloon into catheter 22, e.g., using a heat bond, to reduce or eliminate leakage of fluid through spaces formed between an outer surface of catheter 22 and clover or lobe-shaped protrusions 60 of balloon 24, as described in further detail below.

As shown in FIG. 2, catheter 22 preferably comprises a hollow tubular member having lumen 52 formed therein. Lumen 52 spans from a proximal end to a distal end of catheter 22 and may be configured to receive a wire guide and/or other medical components. In one exemplary method of use, a wire guide may be delivered percutaneously to a site of a vascular condition, and balloon catheter 20 may be delivered over the wire guide by placing the distal end of catheter 22 over the wire guide and advancing balloon catheter 20 distally while balloon 24 is in a deflated state. An inflation lumen extends along a substantial portion of the longitudinal length of catheter 22 and is placed in fluid communication with interior region 55 of balloon 24 to enable inflation and deflation of balloon 24.

Referring still to FIG. 2, a transverse cross-sectional view depicts balloon 24 comprising inner surface 28, outer surface 29, and thickness $t_1$ formed between the inner and outer surfaces. As will be explained in further detail below, outer surface 29 is substantially cylindrical after formation in a balloon mold, and further is substantially cylindrical in the inflated state during treatment of a vessel, since it is formed in balloon mold 200 having a substantially cylindrical interior surface. Moreover, inner surface 28 is non-cylindrical, due to the shape of balloon preform 124, to vary the thickness $t_1$ of balloon 24 around at least a portion of its circumference. The non-uniform thickness may allow the balloon to achieve a reduced diameter profile, for example, by promoting folding of the balloon into at least two wings in the deflated state, as explained in further detail below.

Balloon 24 comprises at least one relatively thick section 32 and at least one relatively thin section 42 disposed about a portion of the circumference of balloon 24. In the embodiment of FIGS. 1-2, balloon 24 comprises three relatively thick sections and three relatively thin sections. Each relatively thin section of the balloon is disposed circumferentially adjacent to one or more relatively thick sections of the balloon. More specifically, relatively thin section 42 is formed between relatively thick sections 32 and 34, relatively thin section 44 is formed between relatively thick sections 34 and 36, and relatively thin section 46 is formed between relatively thick sections 36 and 32. As depicted in FIG. 2, each relatively thick section 32, 34 and 36 comprises a greater thickness $t_1$ compared to each relatively thin section 42, 44 and 46. It will be apparent that while three relatively thick and thin sections are depicted, greater or fewer may be employed.

In the embodiment of FIGS. 1-2, a plurality of clover or lobe-shaped protrusions 60 are formed in a portion of inner surface 28 of balloon 24 to define a portion of the shape of relatively thin sections 42, 44 and 46. As will be explained below, clover or lobe-shaped protrusions 60 correspond to clover or lobe-shaped protrusions 160 of balloon preform 124 (see FIG. 3). The protrusions 160 of balloon preform 124 may be substantially proportionally stretched or expanded, for example, by blow-molding, to form corresponding protrusions 60, as depicted in FIG. 2. In effect, clover or lobe-shaped protrusions 60 reduce the thicknesses $t_1$ of relatively thin sections 42, 44 and 46 of balloon 24.

While clover or lobe-shaped protrusions are depicted, alternative shapes may be formed within inner surface 28 of balloon 24. For example, rectangular-shaped protrusions may be formed within relatively thin sections 42, 44 and 46, such that the junctions between the relatively thin and thick sections are formed at substantially right angles.

Figure 3:
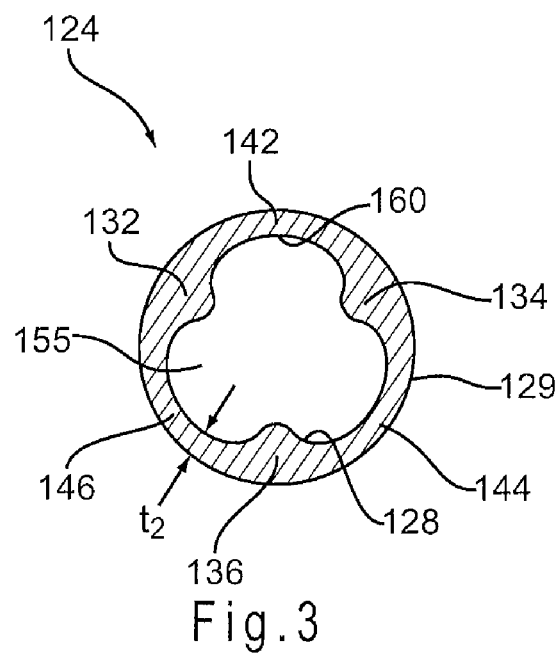
FIG. 3 is a cross-sectional view of a balloon preform that may be used to form the balloon of FIGS. 1-2.

Referring now to FIG. 3, a balloon preform, which may be used to form balloon 24 of FIGS. 1-2, is depicted. In FIG. 3, balloon preform 124 comprises inner surface 128, outer surface 129, and thickness $t_2$ formed between inner and outer surfaces 128 and 129. Like balloon 24 of FIG. 2, balloon preform 124 comprises three relatively thick sections 132, 134 and 136 formed about a portion of the circumference of balloon preform 124. The three relatively thick sections 132, 134 and 136 are separated by three relatively thin sections 142, 144 and 146, as shown in FIG. 3. As noted above, clover or lobe-shaped protrusions 160 may be formed in portions of each of relatively thin sections 142, 144 and 146 to form their reduced thickness shapes.

Balloon preform 124 may be manufactured from a single piece of tubing that is extruded to form the cross-sectional shape depicted in FIG. 3. In particular, the extrusion technique forms the three relatively thick sections 132, 134 and 136 separated by the three relatively thin sections 142, 144 and 146, while outer surface 129 remains substantially cylindrical. Alternatively, the cross-sectional shape of balloon preform 124, as shown in FIG. 3, may be formed by techniques other than extrusion.

Figure 4:
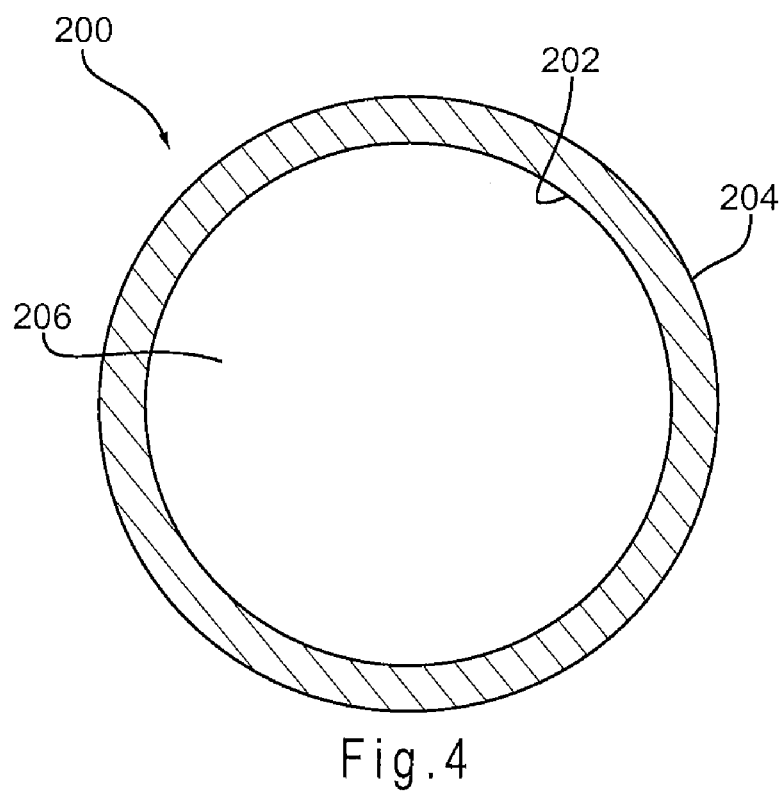
FIG. 4 is a cross-sectional view of an exemplary balloon mold suitable for use with the balloon preform of FIG. 3.

Referring now to FIG. 4, a transverse cross-sectional view of an exemplary balloon mold that may be used to form balloon 24 from balloon preform 124 is shown. As shown in FIG. 4, balloon mold 200 comprises substantially cylindrical interior and exterior surfaces 202 and 204, respectively, and interior space 206 formed therein. Balloon mold 200 may be manufactured using a metal, such as stainless steel, or another suitable material.

Balloon preform 124 preferably is heat-set into the shape of balloon 24 using blow-molding techniques. In one exemplary blow-molding method, a first longitudinal end of balloon preform 124 is sealed, while compressed air is injected into interior space 155 via an open, second longitudinal end of balloon preform 124. The compressed air provides a constant pressure upon inner surface 128 of balloon preform 124. Balloon mold 200 then may be heated by a heat supply that is in proximity to, but not in direct contact with, balloon mold 200. After a warmup period, the compressed air supply may be switched to a high-pressure mode, and may supply the compressed air into interior space 155 for a predetermined period of time.

The heat supply causes balloon preform 124 to stretch. Balloon preform 124 grows progressively and proportionally larger, taking on the stretched balloon shape depicted in FIG. 2. Subsequently, the material of balloon preform 124 is cooled, for example, with compressed air. Balloon preform 124 then may be removed from balloon mold 200. In effect, the shape of balloon preform 124 is substantially proportionally identical to the shape of balloon 24. Further, the substantially cylindrical size and shape of outer surface 29 of balloon 24 corresponds to the cylindrical size and shape of interior surface 202 of balloon mold 200.

Therefore, unlike the balloon of the '224 patent, which formed a non-uniform balloon wall thickness from a cylindrical balloon preform placed in a mold having non-uniform interior surfaces, balloon 24 is formed from balloon preform 124 having a non-uniform thickness and balloon mold 200 having a uniform interior surface 202. Using this technique, balloon 24 comprises a substantially uniform, cylindrical outer surface 29 both after removal from balloon mold 200, and in its inflated state during treatment of a vessel. Moreover, balloon 24 assumes a substantially proportionally identical shape relative to the shape of balloon preform 124. Further, the formation of the non-uniform wall thickness of balloon 24 is not dependent upon an irregular interior surface of balloon mold 200.

For reference purposes, relatively thick sections 132, 134 and 136 of balloon preform 124 of FIG. 3 may comprise a thickness $t_2$ that is about 2-3 times greater than the thickness of relatively thin sections 142, 144 and 146. Relatively thick sections 32, 34 and 36 of balloon 24 of FIG. 2 may comprise a thickness $t_1$ that is about 1.5 to about 2 times greater than the thickness of relatively thin sections 42, 44 and 46. These exemplary dimensions are used for reference purposes only and are not intended to be limiting. The dimensions and ratios of balloon 24 and balloon preform 124 may vary significantly based on the intended use of balloon 24, e.g., whether it is used to treat a hardened fibrous occlusion versus another vascular condition.

In an exemplary method of operation, balloon catheter 20 is delivered into a patient's vessel with balloon 24 in a deflated state, whereby balloon 24 may be folded over itself in a clockwise or counterclockwise fashion to reduce its radial profile. For example, the differential thickness $t_1$ may allow balloon 24 to preferentially fold into a plurality of wings.

When positioned at a desired location, inflation fluid is provided by the inflation lumen to interior region 55 to inflate balloon 24, thereby expanding balloon 24, as depicted in FIG. 1. A vascular condition, such as a stenosis, then may be treated using a central region of balloon 24, i.e., a region formed between tapered proximal and distal regions 25 and 26. Advantageously, the central region of balloon 24 is substantially cylindrical and therefore provides a smooth surface for treating the vascular condition. When the vascular condition has been satisfactorily treated, balloon 24 may be deflated. At this time, balloon 24 may deflate so that relatively thick sections 32, 34 and 26 are drawn inwardly and collapse, thereby allowing relatively thin sections 42, 44 and 46 to be drawn towards one another to form wings.

Additionally, or alternatively, the folding of balloon 24 may occur by proximally retracting balloon catheter 20 into the confines of an outer sheath, which may be disposed coaxially over catheter 22. More specifically, as balloon 24 is retracted into the outer sheath, tapered proximal region 25 engages the outer sheath. Due to the non-uniform thickness configuration of balloon 24, further retraction of balloon 24 into the outer sheath will cause balloon 24 to contract and fold in a more orderly fashion. Therefore, by using non-uniform thickness balloon 24, a reduced cross-sectional balloon profile may be achieved in the deflated state, as opposed to balloons that may not collapse completely and may be difficult to retrieve.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. Apparatus suitable for treating a vascular condition, the apparatus comprising:
 a balloon having an inner surface and an outer surface;
 at least one relatively thin section having a first thickness formed between a portion of the inner surface and the outer surface; and
 at least one relatively thick section having a second thickness formed between a portion of the inner surface and the outer surface, wherein the second thickness is greater than the first thickness,
 wherein the outer surface of the balloon comprises a substantially cylindrical outer diameter after formation in a balloon mold in a state prior to inflation, and further comprises a substantially cylindrical outer diameter in an inflated state.

2. The apparatus of claim 1 wherein the substantially cylindrical outer surface of the balloon corresponds to an interior shape of the balloon mold used to form the balloon.

3. The apparatus of claim 1 wherein the relatively thick section of the balloon is disposed circumferentially adjacent to the relatively thin section of the balloon.

4. The apparatus of claim 1 wherein the balloon comprises three relatively thin sections and three relatively thick sections, wherein each relatively thin section of the balloon is disposed circumferentially between two relatively thick sections.

5. The apparatus of claim 1 wherein a variable thickness formed between the relatively thin section of the balloon and the relatively thick section of the balloon facilitates folding of the balloon into at least two wings in a deflated state.

6. The apparatus of claim 1 wherein the balloon is formed from a balloon preform, wherein a shape of the balloon preform is substantially proportionally identical to a shape of the balloon after formation in the balloon mold.

7. The apparatus of claim 6 wherein the at least one relatively thin section and at the at least one relatively thick section of the balloon corresponds to a proportional shape of the balloon preform.

8. A method for forming a balloon suitable for treating a vascular condition, the method comprising:
providing a balloon preform comprising an inner surface, an outer surface, at least one relatively thin section having a first thickness formed between a portion of the inner surface and the outer surface, and at least one relatively thick section having a second thickness formed between a portion of the inner surface and the outer surface, wherein the second thickness is greater than the first thickness; and
forming the balloon preform into a balloon using a balloon mold comprising a substantially cylindrical interior surface,
whereby the balloon, after formation, comprises an inner surface, an outer surface, at least one relatively thin section having a first thickness formed between a portion of the inner surface and the outer surface of the balloon, and at least one relatively thick section having a second thickness formed between a portion of the inner surface and the outer surface of the balloon, wherein the second thickness is greater than the first thickness.

9. The method of claim 8 wherein the balloon is formed in the balloon mold using a blow-molding technique.

10. The method of claim 8 wherein the outer surface of the balloon comprises a substantially cylindrical outer diameter both after removal from the balloon mold, and in an inflated state during treatment of the vascular condition.

11. The method of claim 8 wherein the relatively thick section of the balloon is disposed circumferentially adjacent to the relatively thin section of the balloon to promote folding of the balloon in a deflated state.

12. The method of claim 8 further comprising extruding the balloon preform to form the relatively thin section and the relatively thick section of the balloon preform, while maintaining a substantially cylindrical outer surface of the balloon preform.

13. The method of claim 8 wherein a shape of the balloon preform is substantially proportionally identical to a shape of the balloon after the balloon is formed in the balloon mold.

* * * * *